United States Patent
Conlon et al.

(10) Patent No.: US 8,821,423 B2
(45) Date of Patent: Sep. 2, 2014

(54) COMPLIANCE STRAPPING

(75) Inventors: Kevin Conlon, Cork (IE); David Sheehan, Waterford (IE); Kerry Meehan, Leitrim (IE)

(73) Assignee: Fastform Research Ltd. (IE)

( * ) Notice: Subject to any disclaimer, the term of this patent is extended or adjusted under 35 U.S.C. 154(b) by 947 days.

(21) Appl. No.: 12/413,798

(22) Filed: Mar. 30, 2009

(65) Prior Publication Data
US 2009/0281469 A1 Nov. 12, 2009

(51) Int. Cl.
| | |
|---|---|
| A61F 5/37 | (2006.01) |
| A61B 19/00 | (2006.01) |
| A45C 13/10 | (2006.01) |
| A45C 13/18 | (2006.01) |
| B65D 27/30 | (2006.01) |
| G09F 3/03 | (2006.01) |
| B65D 33/34 | (2006.01) |
| B65D 55/06 | (2006.01) |
| A61F 5/00 | (2006.01) |
| A61F 5/01 | (2006.01) |

(52) U.S. Cl.
CPC ............... *A61F 5/01* (2013.01); *Y10S 206/807* (2013.01)
USPC ............... 602/3; 128/846; 128/869; 128/870; 128/876; 206/1.5; 206/807; 292/307 R; 292/325; 602/4; 602/5

(58) Field of Classification Search
USPC ........... 128/846, 869, 870, 873–883; 206/1.5, 206/807; 292/307 R, 317–321, 325; 602/3, 602/4, 5, 18–30
See application file for complete search history.

(56) References Cited

U.S. PATENT DOCUMENTS

| | | | | | |
|---|---|---|---|---|---|
| 1,615,057 | A | * | 1/1927 | Tyden ............................ | 292/315 |
| 3,059,359 | A | * | 10/1962 | Goldammer et al. ........... | 40/633 |
| 4,226,036 | A | * | 10/1980 | Krug ................................. | 40/633 |
| 4,783,917 | A | * | 11/1988 | Smith et al. ..................... | 40/633 |
| 4,802,667 | A | * | 2/1989 | Altner ............................. | 482/93 |
| 5,002,212 | A | * | 3/1991 | Charleton ...................... | 224/221 |
| 5,452,930 | A | | 9/1995 | Morgan | |
| 5,547,462 | A | * | 8/1996 | Lanigan et al. .................. | 602/19 |
| 5,581,810 | A | * | 12/1996 | Yewer, Jr. ............................ | 2/44 |
| 5,806,087 | A | * | 9/1998 | Grotefend ............................. | 2/1 |
| 5,979,095 | A | * | 11/1999 | Schneider et al. .............. | 40/633 |

(Continued)

FOREIGN PATENT DOCUMENTS

| | | |
|---|---|---|
| WO | WO2006027763 | 3/2006 |
| WO | WO2008412125 | 4/2008 |

*Primary Examiner* — Michael Brown
*Assistant Examiner* — Brandon L Jackson
(74) *Attorney, Agent, or Firm* — One3 IP Management, P.C.; Jeromye V. Sartain

(57) ABSTRACT

A compliance strapping includes a predetermined adjustability, tamper deterring and indicating strapping, adapted, in use, to form an encircling loop. The compliance strapping is passed around an object and for further security the strap can be threaded through lining material or through a wearable article or medical device. The free end of the elongate member is passed through the loop, which may be a D-loop sewn into the strapping, thus forming an encircling loop of strapping. The second end is brought around to close proximity with a region of the strapping which has been passed through the loop and the tamper indicating means fastened known as the self locking rivet to said region of the strapping. Thus the encircling loop cannot be broken because the region of the strapping with the self locking rivet fastened thereto cannot pass back through the D-loop.

36 Claims, 1 Drawing Sheet

(56) References Cited

U.S. PATENT DOCUMENTS

| | | | | |
|---|---|---|---|---|
| 6,055,756 | A * | 5/2000 | Aoki | 40/633 |
| 6,116,666 | A * | 9/2000 | Adamson et al. | 292/307 R |
| 6,880,717 | B1 * | 4/2005 | O'Conor | 220/318 |
| 6,964,644 | B1 * | 11/2005 | Garth | 602/19 |
| 7,201,410 | B1 * | 4/2007 | Lassen | 292/307 R |
| 7,287,491 | B2 * | 10/2007 | Zents et al. | 119/863 |
| 7,712,155 | B1 * | 5/2010 | Pantoja | 2/321 |
| 7,895,675 | B2 * | 3/2011 | Curphey | 2/338 |
| 7,946,065 | B2 * | 5/2011 | Ali et al. | 40/633 |
| 8,375,522 | B2 * | 2/2013 | York et al. | 24/16 PB |
| 2003/0098027 | A1 * | 5/2003 | Mori | 128/876 |
| 2004/0111942 | A1 * | 6/2004 | Stonehocker | 40/661.06 |
| 2008/0154164 | A1 * | 6/2008 | Sheehan et al. | 602/7 |

* cited by examiner

COMPLIANCE STRAPPING

CROSS-REFERENCE TO RELATED APPLICATIONS

This invention claims priority of Ireland Patent Application No. S2008/0366, filed May 12, 2008, titled Strapping Compliance.

BACKGROUND OF THE INVENTION

This invention relates to an adjustable tamper evident security strap, integrally formed fastening means and to the use thereof.

Many flexible materials have been proposed for use as strapping, including leather, woven and non-woven fabrics, knitted fabrics and synthetic plastics materials. To be used as strapping such materials are provided in elongate forms together with means for attaching one end of the strap to an intermediate region of strap or to the other end of the strap. The attachment means usually comprises two co-operating means whereby one is retained by or secured to the other. For example a buckle or press stud, may be attached to the strap and adapted to adjustably co-operate with receiving means, for example a series of holes or cups, formed or attached to the intermediate region of the strap. In a well known alternative, the strap may be made of, or have attached thereto, attachment means in the form of "Hook and Loop" fastenings. Such materials are sold under the trademark "VELCRO".

The use of strapping both as a tamper-evident seal and as a means to secure objects or parts of the same object such as a suitcase is well known. For example, U.S. Pat. No. 5,452,930 discloses a tamper indicating device which, inter alia, is in the form of a security strap secured, at one end to part of a container or other item. The other, free, end of the strap is passed through a loop secured to another item or part of the item, folded back on itself and secured to the first item or part thereof at the point where the first end is secured. The two ends of the strap are trapped in a unit and cannot be released there from without damaging a permanent visual indicator.

Often, however, it is desired to adjust the strapping tightness such as described above without tampering with the integrity of the looped strap. One example of this desired use is a "compliance strap" which is used to deter removal of and indicate if unauthorised removal or movement of a body supporting member such as a splint or a wearable article has occurred.

In our prior application WO/2006/027763 there is described a conformable splinting device inter alia comprising a sheet of thermoplastic material bonded to a skin contacting fabric layer wherein the thermoplastic sheet is configured to be both flexible and extensible when heated to a softening temperature and wherein the skin contacting layer is adapted to conform to the configuration of the thermoplastic sheet when applied around a body part.

Body supporting devices of the above type may be further adapted to permit removal from around the body portion readily and without the need for mechanical destruction of the device. Thus such devices, which conform to the shape of the body part, may be easily removed and reused.

In our published application WO/2008/041215 we describe a conformable body supporting device which is volumetrically adjustable to accommodate changes such as a reduction in swelling of the body portion covered by the device. Also described therein is a tamper indicating means for indicating unauthorised movement or removal of the device.

This property of ready removal and refuse, while being of benefit to both the medical practitioner and patient, may result in problems of a different nature.

When the medical practitioner first applies the splint in its flexible and extensible state, the damaged body portion is usually manipulated to ensure that the splint "sets" in a configuration which will properly support the body portion. Due to its construction the patient will be able to readily remove the splint without medical supervision, for example because it becomes uncomfortable or wet. Such an unsupervised action may have unfortunate consequences both in medical terms for the patient and in legal terms for the medical practitioner if the body portion is incorrectly supported during the healing process.

BRIEF SUMMARY OF THE INVENTION

The present invention seeks to solve this problem by an arrangement whereby strapping used to secure a splint or a wearable article may have the ends of the strapping secured together with a tamper evident seal and yet the circumference of the strapping loop may be adjusted within a predetermined range. Absence or destruction of such a "compliance strap" indicates unauthorised tampering or removal of a device or wearable article.

In accordance with the present invention there is provided predetermined adjustability, tamper deterring and indicating strapping, adapted, in use, to form an encircling loop, comprising:

a flexible elongate member having a first free end and a second end having detachable tamper indicating means provided adjacent and adapted to be non realisably fastened to the elongate member in the region intermediate the ends, and an upstanding loop member extending from one surface of the member in the region adjacent the second end and intermediate the tamper-indicating means and the first end, wherein said loop member is adapted to receive the first end and permit passage of the elongate member there through but not to permit passage there through of the tamper indicating means when fastened to said elongate member.

The present invention further provides an article of wear incorporating an adjustable tamper evident strapping as herein described.

The article of wear may be a body supporting member such as a splint, brace or cast which may be volumetrically adjustable.

In use, the strapping is passed around the object and for further security the strap can be threaded through the lining material or through the wearable article or medical device itself. The free end of the elongate member is passed through the loop, which may be a D-loop sewn into the strapping, thus forming an encircling loop of strapping. The second end is brought around to close proximity with a region of the strapping which has been passed through the loop and the tamper indicating means fastened known as the self locking rivet to said region of the strapping. Thus the encircling loop cannot be broken because the region of the strapping with the self locking rivet fastened thereto cannot pass back through the D-loop.

The final locking position of the self locking rivet is carried out by the practitioner not the manufacturer. The self locking rivet is physically located at a predetermined distance from the D-loop. This is to aid the practitioner when applying the strap to ensure that when the strap is fixed around the wearable article that the strap can subsequently be loosened by a predetermined amount to compensate for swelling. However the predetermined amount of slackness built into the strap is not enough to enable the patient to remove the strap over the joint (e.g. hand, foot or knee) without physically destructing the strap thus making it evident to the practitioner that unauthorised tampering or removal has taken place. The device cannot be removed without removal of the strap. To remove the strap/device, the self locking rivet must be destroyed or the main strap cut/destroyed. This indicates non compliance or early removal of the device.

The self locking rivet is conveniently located in a sub-strap which may be manufactured from a flexible plastics material such as polyvinyl chloride and which is attached to the main strap. Both ends of the self locking rivet are integrated on the sub-strap so no assembly with small plastic components is required by the user. The sub-strap acts as an aid to guide the practitioner during the application as the design of the strap identifies optimal placement and the predetermined range for subsequent adjustment. The strap is attached together by means of a hook and loop arrangement not the compliance piece or self locking rivet, which enables the strap to be adjusted within a predetermined range.

Tightening or loosening of the strapping may be achieved by moving the free end of the elongate member away from or towards the loop member and securing the new position by attaching the free end to the underlying portion of the encircling strapping loop.

To allow the strap to be tensioned further than the predetermined amount post application a rupture slit enables the PVC sub-strap to break so that the main strap can be tensioned as desired and also indicating to the practitioner that further adjustment was made.

Preferably, means are provided to permit the encircling strapping loop to be tightened or loosened, the amount of adjustment being limited by the location of the tamper indicator. Tightening or loosening of the strapping may be achieved by moving the free end of the elongate member away from or towards the loop member and securing the new position by attaching the free end to the underlying portion of the encircling strapping loop.

The free end of the strapping may be secured to the surface of the elongate member by modifying the surface of the strapping which opposite to that from which the loop member extends to permit the surface at the free end to adhere to another part of the same surface when the two are brought into contact. The parts of surface may be adhered to each other using a conventional "hook and loop" fastening system such as that sold under the trade name VELCRO, or by any other known fastening system such as a mushroom fastener. Such modification may be achieved by providing a layer of hook fabric on the elongate member toward the free end thereof and a second layer of loop material on the same surface but toward the second end. Preferably, the hook and loop layers abut each other.

BRIEF DESCRIPTION OF THE DRAWINGS

The invention will be described in greater detail with reference to the accompanying drawings in which.

DETAILED DESCRIPTION OF THE INVENTION

Figure 1:
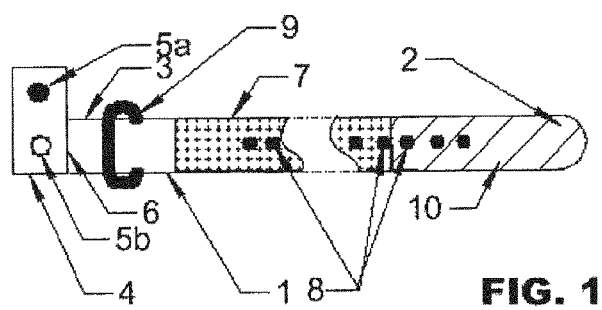
FIG. 1 is a schematic plan view of one side of the strapping of the invention, prior to use.
Figure 2:
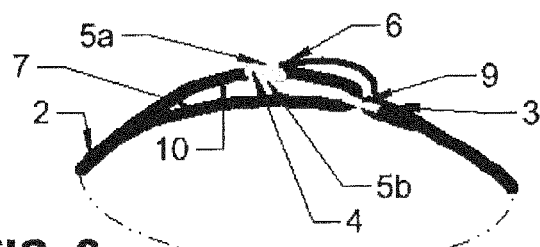
FIG. 2 is schematic elevation view depicting the strapping of the invention as first formed into a sealed loop and initially tightened.

Referring to FIG. 1, strapping is formed from a flexible fabric material layer 1 which has a free end 2 and a remote end to which is attached a sub-strap 3 to which is releasably attached a tab 4. Tab 4 carries the complementary parts 5*a* and 5*b* of the tamper evident self locking rivet. Tab 4 is separable from the remainder of the sub strap by rupturing the weakened area or fail line 6.

The region of the strapping intermediate the ends carries a layer 7 of a loop fabric. A layer 10 of a hook fabric, carried on the same surface of the strapping, extends from the free end 2. Suitable hook and loop fabrics for use in the invention may be those such as that sold under the trade name VELCRO. A plurality of holes 8 are also punched through the fabric layer 1 and the co-extensive overlying hook 10 and loop 7 layers.

The complementary components 5*a* and 5*b* are adapted to be permanently bonded to each other when brought into contact. The self locking rivet may be a snap fastener of the press stud type in which both parts are made of a fusible material.

A D-loop 9 is attached to or formed in the fabric of the reverse side of the strapping that carries the hook and loop layers and is located adjacent the remote end 3. The strapping may be strengthened to facilitate passage through loop 9 for example by adding a layer of a stiffening material to the strapping fabric in the region of the free end 2.

Figure 3:
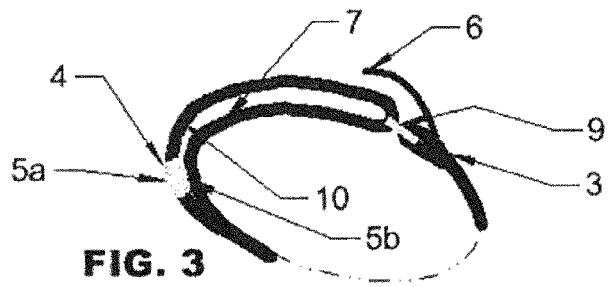
FIG. 3 is a view similar to that shown in FIG. 2 except that the strap has been tightened without disturbing the self locking rivet.

In use, as shown in FIG. 3, the strapping is passed around the object (not shown) to be secured, for example a splint applied around a forearm. The free end 2 of the strapping is passed through loop 9 and the strap tightened around the object. Tab 4 is wrapped over the strapping which has been passed through the loop and the components 5*a* and 5*b* are connected to each other via one of the holes 8 and permanently bonded together, for example by fusing. The free end 2 is then doubled back over loop 9 and brought into proximity with the intermediate section of the strapping such that the now facing hook and loop layers can contact each other.

The strapping can be tightened or loosened by separating the hook and loop layers and sliding the strapping through the loop before re-attaching the hook and loop layers in the new position. The strapping can only be loosened to the point where the bonded components 5*a* and 5*b* abut, but do not pass through the loop. The bonded components 5*a* and 5*b* form the self locking rivet since the strapping loop cannot be broken unless the free end 2 can be passed back through loop 9.

Figure 4A:
FIGS. 4*a* and 4*b* are plan schematic plan views of embodiments of the present invention.
Figure 4B:
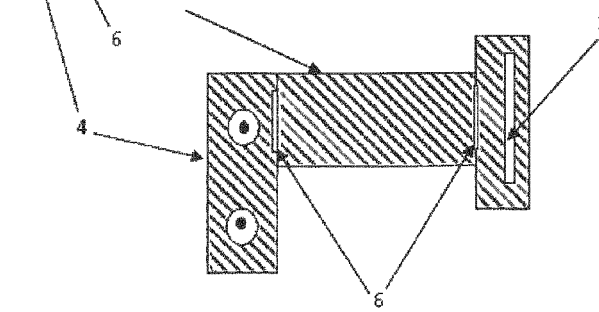

Preferably the sub-strap is bonded to the main strap, however the sub-strap 3 can also be attached by threading the main strap through a slit 11 in the sub strap as shown in FIGS. 4*a* and 4*b*. This allows the physician the option of reintroducing a compliance strap element as the original may have been destructively removed due to tampering or medical examination. The use of the replacement sub-strap prevents the need to dispose of the main strap once compliance feature has been removed.

Although the tamper indicating strapping of the present invention has applications in many fields, it is particularly useful in the medical field for the detection of unauthorized adjustment or removal of medical devices such as splints, braces and casts which been applied by practitioners. Additionally, the strap configuration enables a physician to intuitively (without measuring or instructions) to set the strap on application with a predetermined length of extra strap, which facilitates loosening to a maximum predefined strap length. The length of the sub-strap, i.e. the distance between the tamper evident self-locking rivet assembly and the D-loop defines the range over which the strap can be set on application. Typically this distance will be about 10-25 mm.

The maximum loosening range is pre-defined and set in the strap at manufacture to ensure that the maximum strap length permissible will still prevent the strap from passing over a joint such as with a hand, knee or foot. After application, there is no limit on the amount the strap can be tightened. This is due to a rupture slit that enables the strap to be tightened further from the D-loop than the original position that the self locking rivet was positioned on application of the wearable article.

What is claimed as new and desired to be protected by Letters Patent of the United States is:

1. An adjustable tamper evident strapping, adapted, in use, to form an encircling loop, comprising:
    a flexible elongate member having a first free end, a second end, and a plurality of holes between the ends;
    a detachable tamper indicating means attached to the second end and comprising a main portion and a folding portion that is capable of folding over the main portion and providing a tamper proof connection between the main and folding portions and through one of the plurality of holes;
    an upstanding loop member extending from one surface of the member in the region adjacent the second end and intermediate the tamper-indicating means and the first end; and
    wherein said loop member is adapted to receive the first end and permit passage of the elongate member there through but not to permit passage there through of the tamper indicating means when fastened to said elongate member; and
    the flexible elongate member further comprising cooperating connection sections located so that after the first free end of the elongate member is permitted passage through the loop member, the first free end can be releasably connected to the elongate member intermediate the first and second ends.

2. The adjustable tamper evident strapping as claimed in claim 1, further comprising an article of wear.

3. An article as claimed in claim 2 in the form of a body supporting member.

4. An article as claimed in claim 1 wherein the connection sections comprise cooperating hook and loop sections on the first free end and the elongate member.

5. A compliance strap comprising:
    a flexible material layer having a free end, a remote end, and a mid-section;
    the remote end having a sub-strap adapted to be non-releasably fastened to the material layer in mid-section;
    a loop attached to the mid-section of the material layer, the loop allowing for passage there through of the material layer but not the fastened sub-strap; and
    a releasable fastener comprising a first fastener component attached in a position proximate to the free end and a second fastener component attached to the mid-section.

6. The compliance strap of claim 5, wherein the sub-strap comprises a fail line.

7. The compliance strap of claim 6, wherein the sub-strap comprises a press stud fastener.

8. The compliance strap of claim 7, wherein the press stud fastener is formed from a fusible material.

9. The compliance strap of claim 8, wherein the releasable fastener comprises a hook and loop fastener.

10. The compliance strap of claim 8, wherein the releasable fastener comprises a mushroom fastener.

11. The compliance strap of claim 7, wherein the releasable fastener comprises a hook and loop fastener.

12. The compliance strap of claim 7, wherein the releasable fastener comprises a mushroom fastener.

13. The compliance strap of claim 6, wherein the sub-strap comprises a self-locking rivet.

14. The compliance strap of claim 6, wherein the releasable fastener comprises a hook and loop fastener.

15. The compliance strap of claim 14, wherein the first fastener component comprises a hook material.

16. The compliance strap of claim 14, wherein the first fastener component comprises a loop material.

17. The compliance strap of claim 6, wherein the releasable fastener comprises a mushroom fastener.

18. The compliance strap of claim 5, wherein the sub-strap comprises a self-locking rivet formed on a tab of the sub-strap and configured to be fastened within any of a plurality of holes formed in the mid-section of the material layer with the tab folded thereabout and once so fastened to not be capable of passing through the loop.

19. The compliance strap of claim 18, wherein the releasable fastener comprises a hook and loop fastener.

20. The compliance strap of claim 18, wherein the releasable fastener comprises a mushroom fastener.

21. The compliance strap of claim 5, wherein the sub-strap comprises a press stud fastener.

22. The compliance strap of claim 21, wherein the press stud fastener is formed from a fusible material.

23. The compliance strap of claim 22, wherein the releasable fastener comprises a hook and loop fastener.

24. The compliance strap of claim 22, wherein the releasable fastener comprises a mushroom fastener.

25. The compliance strap of claim 21, wherein the releasable fastener comprises a hook and loop fastener.

26. The compliance strap of claim 21, wherein the releasable fastener comprises a mushroom fastener.

27. The compliance strap of claim 13, wherein the releasable fastener comprises a hook and loop fastener.

28. The compliance strap of claim 13, wherein the releasable fastener comprises a mushroom fastener.

29. The compliance strap of claim 5, wherein the releasable fastener comprises a hook and loop fastener.

30. The compliance strap of claim 29, wherein the first fastener component comprises a hook material.

31. The compliance strap of claim 29, wherein the first fastener component comprises a loop material.

32. The compliance strap of claim 5, wherein the releasable fastener comprises a mushroom fastener.

33. A method of securing medical devices to deter unauthorized removal of the device, comprising the steps of:
    applying a medical device to the body of a patient;
    applying at least one tamper-evident compliance strap around the medical device, the compliance strap comprising;
    a flexible material layer having a free end, a remote end, and a mid-section;
    the remote end having a sub-strap adapted to be non-releasably fastened to the material layer in mid-section;
    a loop attached to the mid-section of the material layer, the loop allowing for passage there through of the material layer but not the fastened sub-strap; and a releasable fastener comprising a first fastener component attached in a position proximate to the free end and a second fastener component attached to the mid-section;

passing the free end of the compliance strap through the loop attached to the compliance strap; and securing the compliance strap by fastening the sub-strap to the compliance strap.

34. The method of claim 33, wherein the medical device further comprises a splint.

35. The method of claim 33, wherein the medical device further comprises a brace.

36. The method of claim 33, wherein the medical device further comprises a cast.

* * * * *